(12) United States Patent
Waddell

(10) Patent No.: US 10,322,205 B2
(45) Date of Patent: *Jun. 18, 2019

(54) FLEXIBLE ION GENERATION DEVICE

(71) Applicant: Charles Houston Waddell, Roanoke, VA (US)

(72) Inventor: Charles Houston Waddell, Roanoke, VA (US)

(73) Assignee: Global Plasma Solutions, Inc., Savannah, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/816,027

(22) Filed: Nov. 17, 2017

(65) Prior Publication Data

US 2018/0071426 A1    Mar. 15, 2018

Related U.S. Application Data

(63) Continuation of application No. 15/412,825, filed on Jan. 23, 2017, now Pat. No. 9,849,208.

(60) Provisional application No. 62/281,318, filed on Jan. 21, 2016.

(51) Int. Cl.
*A61L 9/22* (2006.01)
*H01J 33/02* (2006.01)

(52) U.S. Cl.
CPC .............. *A61L 9/22* (2013.01); *H01J 33/02* (2013.01); *A61L 2209/16* (2013.01)

(58) Field of Classification Search
CPC ......... A61L 9/22; A61L 2209/16; H01J 33/02
USPC .............. 250/423 R, 424, 423 P, 423 F
See application file for complete search history.

(56) References Cited

U.S. PATENT DOCUMENTS

2009/0211459 A1    8/2009    Hu et al.

*Primary Examiner* — Nicole M Ippolito
*Assistant Examiner* — Hanway Chang
(74) *Attorney, Agent, or Firm* — Seth L. Hudson; Clements Bernard Walker PLLC

(57) ABSTRACT

The present invention provides methods and systems for the flexible ion generation device includes at least one dielectric layer, at least one trace having a first end and a second end, the at least one trace is engaged to the at least one dielectric layer, and at least one emitter engaged to the trace for emitting ions.

20 Claims, 6 Drawing Sheets

FLEXIBLE ION GENERATION DEVICE

CROSS REFERENCE TO RELATED PATENT APPLICATION

This application is a continuation of U.S. patent application Ser. No. 15/412,825 filed Jan. 23, 2017 and entitled "FLEXIBLE ION GENERATION DEVICE", which claims the benefit of U.S. Provisional Patent Application No. 62/281,318, filed on Jan. 21, 2016, and entitled "FLEXIBLE ION ELECTRODE," the contents of which are incorporated in full by reference herein.

FIELD OF THE INVENTION

The present invention relates generally to the field of air treatment, and more particularly to the treatment of air using ionization that is produced using a flexible ion generation device for dispersing the ions into a conduit or a duct.

BACKGROUND OF THE INVENTION

Air and other fluids are commonly treated and delivered for a variety of applications. For example, in heating, ventilation and air-conditioning (HVAC) applications, air may be heated, cooled, humidified, dehumidified, filtered or otherwise treated for delivery into residential, commercial or other spaces.

Needs exist for improved systems and methods of treating and delivering purified air for these and other applications. It is to the provision of improved systems and methods meeting these needs that the present invention is primarily directed.

BRIEF SUMMARY OF THE INVENTION

According to an embodiment of the present invention, the flexible ion generation device includes at least one dielectric layer, at least one trace having a first end and a second end, the at least one trace is engaged to the at least one dielectric layer, and at least one emitter engaged to the trace for emitting ions.

According to another embodiment of the present invention, the flexible ion generation device includes an emitter with a first end and a second end, the first end of the emitter is engaged to the trace and the second end extends away from the trace and contains a point for emitting ions.

According to yet another embodiment of the present invention, the flexible ion generation device includes a trace composed of copper.

According to yet another embodiment of the present invention, the flexible ion generation device includes a first dielectric layer and a second dielectric layer with a trace disposed therebetween.

According to yet another embodiment of the present invention, the flexible ion generation device includes a connector engaged to the first end and the second end of the trace.

According to yet another embodiment of the present invention, the flexible ion generation device includes a brush containing a plurality of bristles, wherein the brush is engaged to the trace.

According to yet another embodiment of the present invention, the flexible ion generation device includes a brush, containing a plurality of bristles, wherein the brush is engaged to the emitter.

According to yet another embodiment of the present invention, the flexible ion generation device includes a first dielectric layer having a top portion, a bottom portion, a top side, a bottom side, a left side, and a right side, and a second dielectric layer having a top portion, a bottom portion, a top side, a bottom side, a left side, and a right side. A trace is positioned between the first dielectric layer and the second dielectric layer. A plurality of emitters are engaged to the trace and extend outward from the trace to either the top side or the bottom side of the first dielectric layer and the second dielectric layer.

According to yet another embodiment of the present invention, the flexible ion generation device includes a point positioned on the emitter for emitting ions.

According to yet another embodiment of the present invention, the flexible ion generation device includes a second dielectric layer with a plurality of openings that are located over a portion of the emitter for allowing ions to be emitted.

According to yet another embodiment of the present invention, the flexible ion generation device includes a brush engaged to the trace for emitting ions.

According to yet another embodiment of the present invention, the flexible ion generation device includes a second trace engaged to the top portion of the second dielectric layer and a third dielectric layer having a top portion and a bottom portion, wherein the bottom portion of the third dielectric layer is engaged to the second trace and the top portion of the second dielectric layer.

According to yet another embodiment of the present invention, the flexible ion generation device wherein the device is mounted adjacent a heat exchanger located within a conduit.

According to yet another embodiment of the present invention, a method of producing ions that includes providing a flexible ion generation device that includes at least one dielectric layer, at least one trace having a first end and a second end, the at least one trace is engaged to the at least one dielectric layer, and at least one emitter engaged to the trace for emitting ions. The flexible ion generation device is mounted within a conduit, and positioning the at least one emitter within the airflow within the conduit.

According to yet another embodiment of the present invention, a method of producing ions that includes a power source engaged to at least one connector.

According to yet another embodiment of the present invention, a method of producing ions that includes mounting the flexible ion generation device after a filter and before a cooling coil.

According to yet another embodiment of the present invention, a method of producing ions that includes at least one brush engaged to the emitter for dispensing ions.

According to yet another embodiment of the present invention, a method of producing ions that includes a connector engaged to the first end and the second end of the at least one trace.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
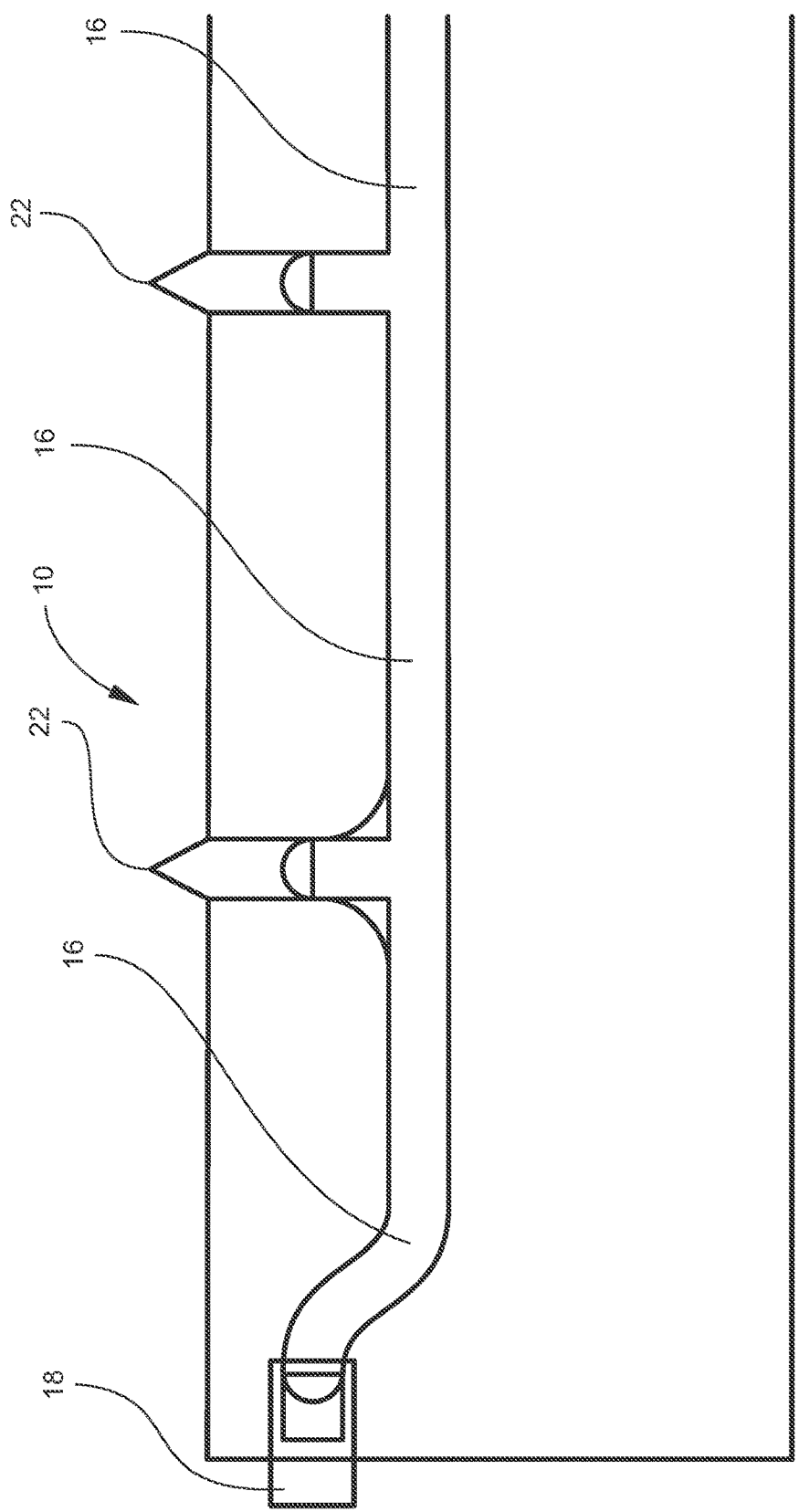
FIG. 1 is a top view of one embodiment of the flexible ion generation device.

Referring now specifically to the drawings, a flexible ion generation device is described herein and illustrated in FIG. 1 and is shown generally at reference numeral 10. The flexible ion generation device 10 has at least a first dielectric layer 12 and, optionally, a second dielectric layer 14. The first dielectric layer 12 contains a top portion, a bottom portion, a top side, a bottom side, a left side, and a right side, wherein the top side and the bottom side are opposed to each other and the left side and the right side are opposed to each other. The second dielectric layer 14 contains a top portion, a bottom portion, a top side, a bottom side, a left side, and a right side, wherein the top side and the bottom side are opposed to each other and the left side and the right side are opposed to each other.

In one embodiment, the flexible ion generation device 10 includes a first dielectric layer 12 having a trace 16 disposed thereon. In another embodiment, the flexible ion generation device 10 includes a first dielectric layer 12 and a second dielectric layer 14 having a trace 16 disposed therebetween (the trace 16 will be considered a first trace when more than one trace is utilized with two or more dielectric layers). The trace 16 has a first end and a second end. The flexible ion generation device 10 may have one or more traces 16, such as copper traces, positioned on the top portion of the first dielectric layer 12. The bottom portion of the second dielectric layer 14 is formed over the trace 16 and coupled to the first dielectric layer 12. It will be appreciated that while the trace 16 as illustrated in FIG. 1 is positioned on the top portion of the first dielectric layer 12, the trace 16 may also be positioned on the bottom side of the second dielectric layer 14, and the first dielectric layer 12 is formed over the trace 16 and coupled to the second dielectric layer 14.

As illustrated in FIG. 1, the trace 16 extends longitudinally along the length of the flexible ion generation device 10. In other words, the trace 16 extends from the left side to the right side of the first dielectric layer 12 and the second dielectric layer 14. The trace 16 contains a first end and a second end, whereby the first end is disposed adjacent the right side of the first dielectric layer 12 and second dielectric layer 14 and the second end is disposed adjacent the left side of the first dielectric layer 12 and the second dielectric layer 14. The first end and the second end of the trace 16 may extend beyond the right side and left side of the first dielectric layer 12 and the second dielectric layer 14. A conductive pad or connector 18 may be disposed on the first end and/or the second end of the trace 16. The connector 14 is engaged to a power supply for supplying power to the flexible ion electrode 10, and more specifically the trace 16.

Figure 2:
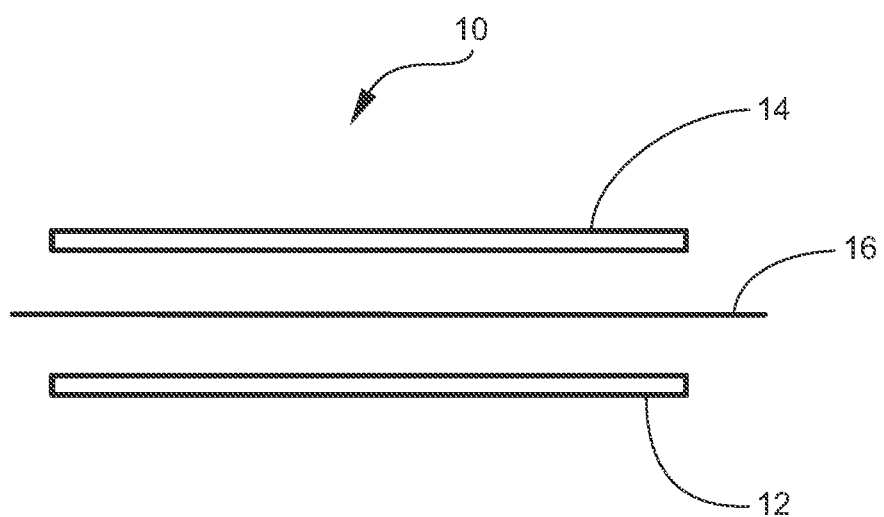
FIG. 2 is an exploded view of one embodiment of the flexible ion generation device.

An emitter 20 may be engaged or etched into the trace 16. As illustrated, the emitter 20 extends to at least the first side and/or second side of the flexible ion electrode 10. As illustrated in FIGS. 1 and 2, the emitter 20 extends to the top side and/or the bottom side of the first dielectric layer 12 and second dielectric layer 14. The emitter 20 extends from the trace 16 to either the top side or bottom side of the first dielectric layer 12 and the second dielectric layer 14. All emitters 20 of the trace can extend to the same side of the dielectric layer, may alternate sides of the dielectric layer, or may extend to different sides of the dielectric layer at different intervals. The first end of the emitter 20 is etched into the trace 16 and the second end of the emitter 20 extends to a point 22. As illustrated, the emitter 20 at the second end has a gradually reducing width that terminates at a sharp point 22, allowing ions to flow therefrom. The point 22 of the emitter 20 is not connected, coupled, or engaged to the first dielectric layer 12 and second dielectric layer 14 and may extend outwards from these layers (12, 14). In other words, the emitter 20 and/or point 22 may extend beyond the top side or bottom side of the first dielectric layer 12 or and second dielectric layer 14. The point 22 may be coated or plated with a corrosion resistant layer such as gold or other coating material.

Figure 3:
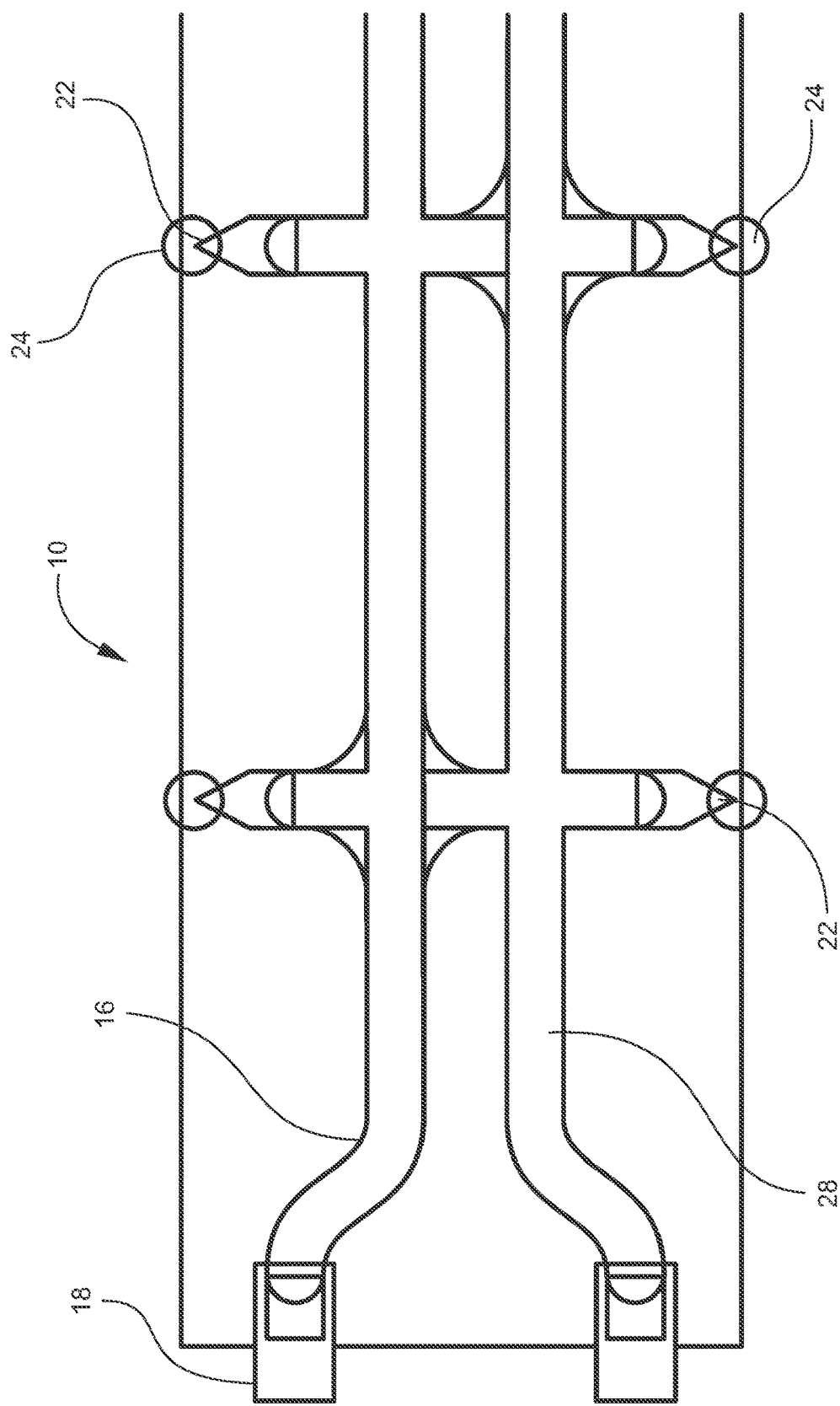
FIG. 3 is a top view of another embodiment of the flexible ion generation device.

The point 22 disposed on the second end of the emitter 20 allows ions to flow therefrom. The trace 16 contains at least one emitter 20, preferably at least two emitters 20, and more preferably a plurality of emitters 20. It is important to note that the first dielectric layer 12 and the second dielectric layer 14 does not cover the point 22, thus allowing ions to flow from the point 22 and into the surrounding area. The dielectric layers (12, 14) adjacent the point may be cut-away, pulled back, or otherwise removed, allowing ions to freely flow from the end of the point 22. In another alternative embodiment, only one dielectric layer may be cut-way, pulled back, or otherwise removed from the point 22 of the emitter. For example and as illustrated in FIGS. 2 and 3, the trace 16 and emitter 20 are disposed on the top portion of the first dielectric layer 12, and the second dielectric layer 14 is formed over the trace 16 and emitter 20 and coupled to the first dielectric layer 12. The point 22 of the emitter 20 does not extend outward from the first dielectric layer 12 and second dielectric layer 14. Instead, the portion of the second dielectric layer that would be cover or be over top the point 22 is cut-away, pulled back, or otherwise removed, forming an opening 24 and allowing ions to emit from the point and into the surrounding area.

In another alternative embodiment, the second dielectric layer 14 may be pre-cut with a portion removed from the top side and/or bottom side in the area where the second dielectric layer 14 will be adjacent or overtop the point 22 forming an opening 24. Therefore, when the second dielectric layer 14 is formed over the trace 16 and emitter 20, the opening 24 is adjacent the point 22, wherein the second dielectric layer 14 does not cover the point 22. In another alternative embodiment, the first dielectric layer 12 and second dielectric layer 14 both are precut with the portion of the respective layer (12, 14) that may be adjacent or overtop the point 22 are removed forming openings 24. Therefore, when the trace 16 and emitter 20 are engaged to the top portion of the first dielectric layer 12, the point 22 is positioned within the opening 24, such that the first dielectric layer 12 will not cover the point 22 and the point 22 is within the opening 24. As the second dielectric layer 14 is formed over the trace 16 and emitter 20, the opening 24 is placed adjacent the point 22, so that the second dielectric layer 14 does not cover the point 22.

An insulating jacket 24 may be positioned over at least a portion of the flexible ion generation device 10. In the cross section shown in FIG. 5, the insulating jacket may encompass the first dielectric layer 12 and second dielectric layer 14 (including trace 16 and a portion of the emitter 20 contained therein). The insulating jacket 24 may surround and protect the dielectric layers (12, 14), including the trace 16 and emitter 20. It should be noted, the insulating jacket 24 does not cover the point 22.

Figure 5:
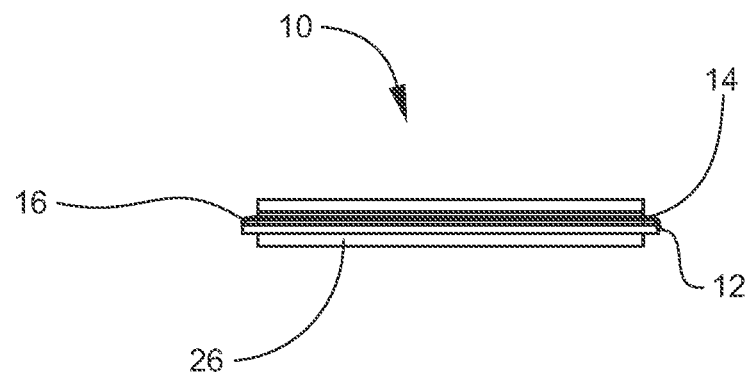
FIG. 5 is a cross-sectional view of another embodiment of the flexible ion generation device.
Figure 6:
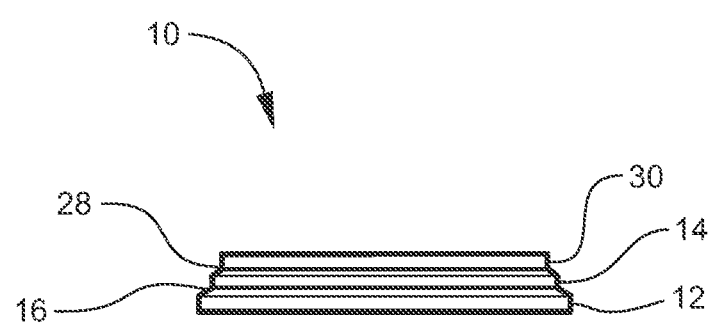
FIG. 6 is a cross-sectional view of another embodiment of the flexible ion generation device.
Figure 7:
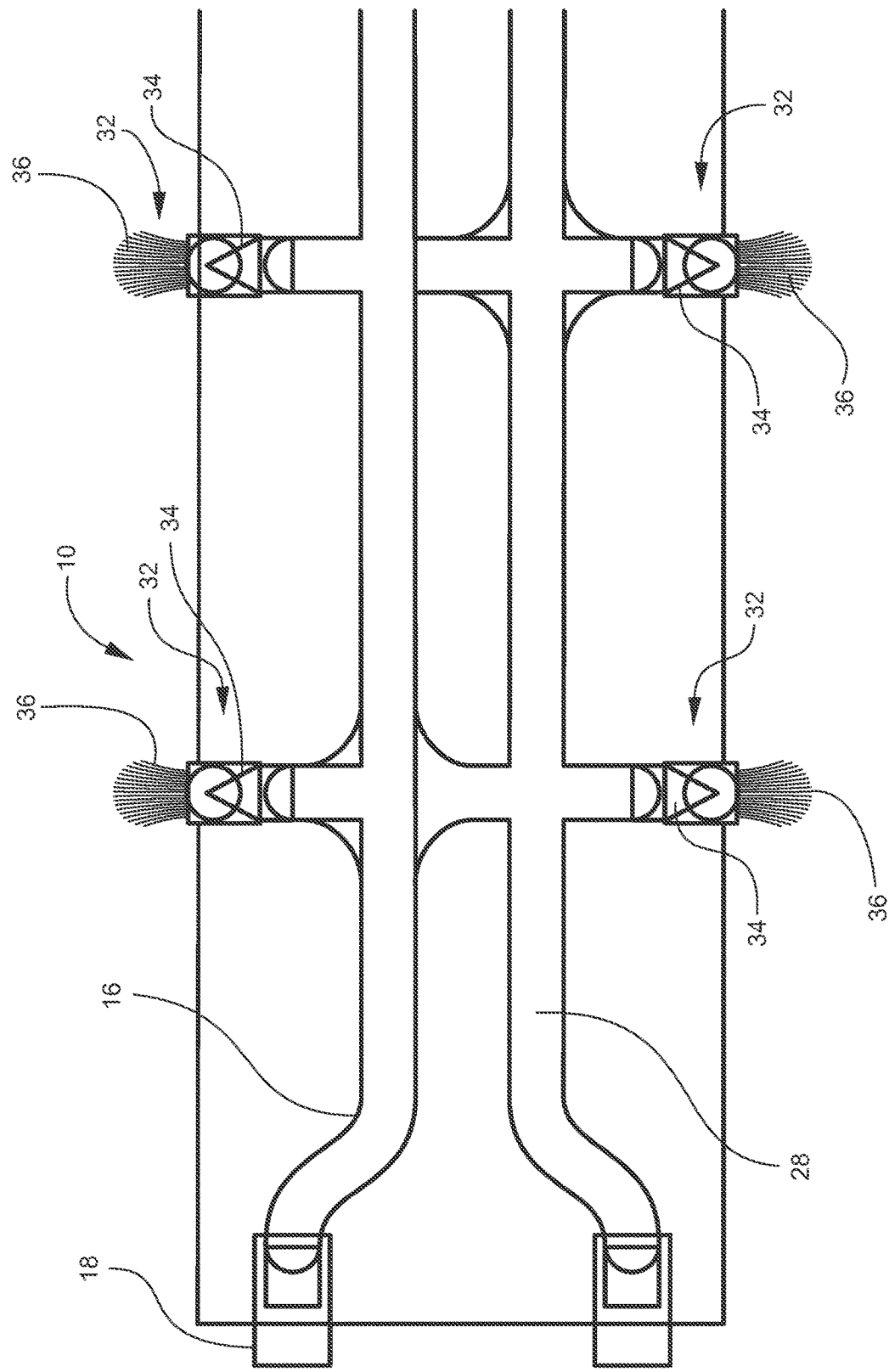
FIG. 7 is a top perspective view of another embodiment of the flexible ion generation device.

In another alternative embodiment and as shown in FIG. 5, the flexible ion generation device 10 may include a second trace 28 and a third dielectric layer 30 (in this embodiment the trace 16 becomes the first trace). The third dielectric layer 30 contains a top portion, a bottom portion, a top side, a bottom side, a left side, and a right side, wherein the top side and the bottom side are opposed to each other and the left side and the right side are opposed to each other.

In this embodiment, the second dielectric layer 14 and third dielectric layer 30 contain the second trace 28 therebetween (and the first trace 16 is disposed between the first dielectric layer 12 and the second dielectric layer 14). The second trace 28 has a first end and a second end. The second trace 28 is positioned on the top portion of the second dielectric layer 14. The bottom portion of the third dielectric layer 30 is formed over the second trace 28 and coupled to the second dielectric layer 14. It will be appreciated that while the second trace 28 may be positioned on the top portion of the second dielectric layer 14, the second trace 28 may also be positioned on the bottom side of the third dielectric layer 30, and the second dielectric layer 14 is formed over the second trace 28 and coupled to the third dielectric layer 30.

Figure 4:
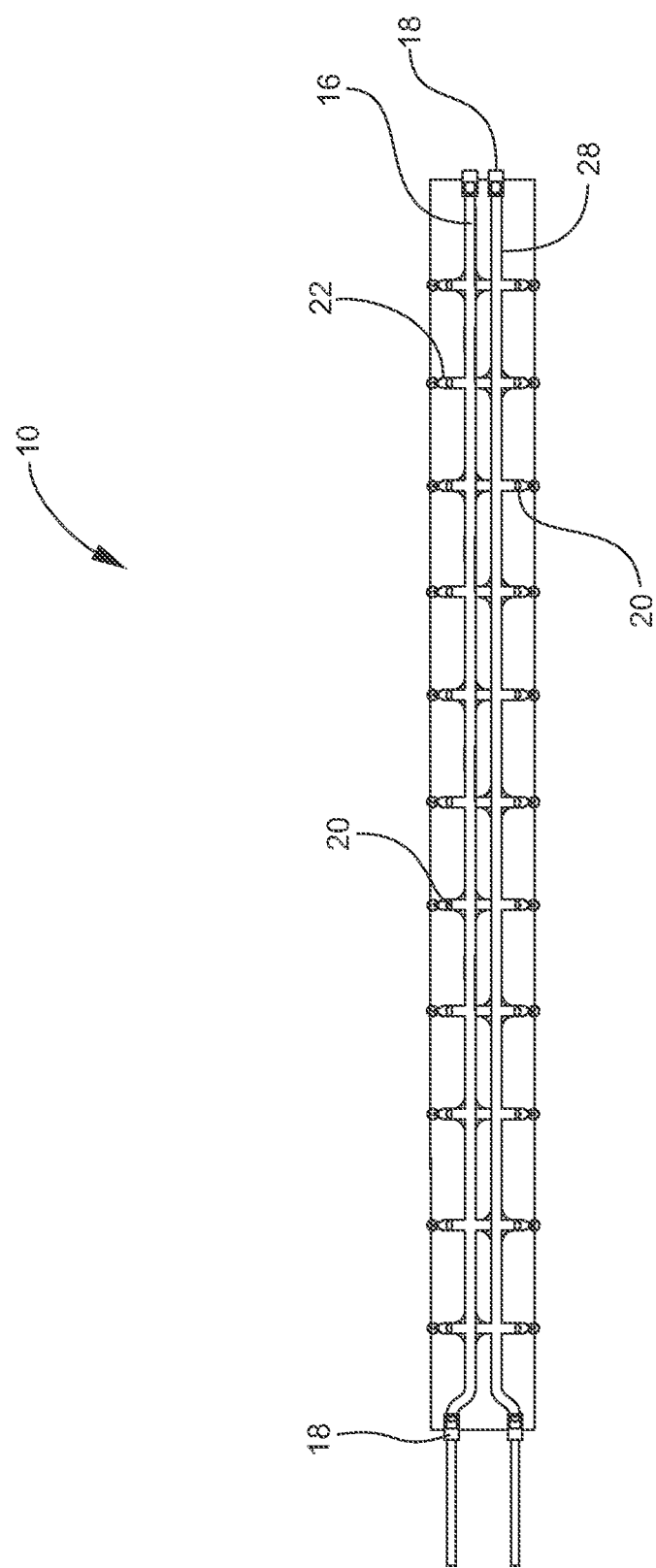
FIG. 4 is a top view of another embodiment of the flexible ion generation device.

As illustrated in FIG. 4, the second trace 28 extends longitudinally along the length of the flexible ion generation device 10. In other words, the second trace 28 extends from the left side to the right side of the second dielectric layer 14 and the third dielectric layer 30. The second trace 28 contains a first end and a second end, whereby the first end is disposed adjacent the right side of the second dielectric layer 14 and third dielectric layer 30 and the second end is disposed adjacent the left side of the second dielectric layer 14 and third dielectric layer 30. The first end and the second end of the second trace 28 may extend beyond the right side and left side of the second dielectric layer 14 and third dielectric layer 30. A conductive pad or connector 18 may be disposed on the first end and/or the second end of the second trace 28. The connector 14 is engaged to a power supply for supplying power to the flexible ion electrode 10, and more specifically, the first trace 16 and second trace 28.

An emitter 20 may be engaged or etched into the second trace 28. As illustrated, the emitter 20 extends to at least the first side and/or second side of the flexible ion electrode 10. As illustrated in FIG. 5, the emitter 20 extends to the top side and/or the bottom side of the flexible ion generation device 10. The emitter 20 extends from the second trace 28 at an angle of about 90° to either the top side or bottom side of the flexible ion generation device 10 and away from the second trace 28. The first end of the emitter 20 is etched into the second trace 28 and the second end of the emitter 20 extends to a point 22. The point 22 of the emitter 20 is not connected, coupled, or engaged to the second dielectric layer 14 and third dielectric layer 30 and extends outwards from these layers (14, 30).

The point 22 disposed on the second end of the emitter 20 allows ions to flow therefrom. The second trace 28 contains at least one emitter 20, preferably at least two emitters 20, and more preferably a plurality of emitters 20. It is important to note that the second dielectric layer 14 and third dielectric layer 30 does not cover the point 22, thus allowing ions to flow from the point 22 and into the surrounding area. The dielectric layers (14, 30) adjacent the point may be cut-away, pulled back, or otherwise removed, allowing ions to freely flow from the end of the point 22. The emitter 20 etched into the second trace 28, extends outward from the second trace 28 and in an opposite direction than the emitter 20 of the first trace 16 extends. In other words, the emitter 20 of the first trace 16 and the emitter 20 of second trace 28 extend in opposite directions and towards opposite sides of the respective dielectric layer (14,30) as illustrated in FIG. 5.

In another alternative embodiment, only one dielectric layer may be cut-way, pulled back, or otherwise removed from the point 22 of the emitter 20. For example and as illustrated in FIG. 5, the second trace 28 and emitter 20 are disposed on the top portion of the second dielectric layer 14, and the third dielectric layer 30 is formed over the second trace 28 and emitter 20 and coupled to the second dielectric layer 14. The point 22 of the emitter 20 does not extend outward from the second dielectric layer 14 and the third dielectric layer 30. Instead, the portion of the third dielectric layer 30 that would cover or be over top the point 22 is cut-away, pulled back, or otherwise removed, forming an opening 24 and allowing ions to emit from the point and into the surrounding area.

In another alternative embodiment, the third dielectric layer 30 may be pre-cut with a portion removed from the top side and/or bottom side in the area where the third dielectric layer 30 will be adjacent or overtop the point 22 forming an opening 24. Therefore, when the third dielectric layer 30 is formed over the trace 16 and emitter 20, the opening 24 is adjacent the point 22, wherein the third dielectric layer 30 does not cover the point 22. The second dielectric layer 14 and the third dielectric layer 30 both are precut with the portion of the respective layer (14, 30) that may be adjacent or overtop the point 22 are removed forming openings 24. Therefore, when the trace 16 and emitter 20 are engaged to the top portion of the second dielectric layer 14, the point 22 is positioned within the opening 24, such that the second dielectric layer 14 will not cover the point 22 and the point 22 is within the opening 24. As the third dielectric layer 30 is formed over the second trace 28 and emitter 20, the opening 24 is placed adjacent the point 22, so that the third dielectric layer 30 does not cover the point 22. Additionally, both sides of the third dielectric layer 30 may have openings on the top side and bottom side, so that the third dielectric layer 30 does not cover the point 22 of the first trace 16.

An insulating jacket 24 may be positioned over at least a portion of the flexible ion generation device 10. The insulating jacket may encompass the first dielectric layer 12, second dielectric layer 14, and third dielectric layer 30 (including the first trace 16, the second trace 28, and a portion of the emitters 20 contained therein). The insulating jacket 24 may surround and protect the dielectric layers (12, 14, 30), including the trace 16 and emitter 20. It should be noted, the insulating jacket 24 may surround and protect the flexible ion generation device 10, while leaving the points 22 unobstructed for allowing the ions to flow freely and the connectors 18 to facilitate coupling of the flexible ion generation device 10 to a power supply.

In other alternative embodiments of the present invention, any number of dielectric layers may be used with or without a conducting trace in-between each dielectric layer.

The dielectric layer may be a polyamide tape, a silicon tape, or the like that has dielectric properties. One suitable tape sold by DuPont is Kapton®. The traces may be formed from any substance that can conduct electricity, such as metal, nickel, gold, copper, or copper with nickel/gold plating.

In another alternative embodiment, the present invention consists of first dielectric layer 12 adjacent a first trace 16 that has a top portion and a bottom portion. The bottom portion of the first trace 16 is connected to the top portion of the first dielectric layer 12 and the top portion of the first trace 16 is engaged to a metal object that is grounded to ground the flexible ion generation device 10.

The connectors 18 of the trace (16, 28) are engaged to a power supply providing alternating current or direct current, with constant or varying frequency, constant or varying voltage and constant or varying current. Multiple flexible ion electrodes 10 may be engaged to each other. In this arrangement, each flexible ion generation device includes a first connector and a second connector, and the second connector of a first flexible ion electrode and the first connector of a second flexible ion electrode are engaged to each other. In one example, a copper trace is disposed on the second connector and first connector for selectively securing the first flexible ion electrode and second flexible ion electrode together. Alternatively, any other conducting metal, composition, or substance may be used.

In another alternative embodiment, a brush 32 may be engaged to the trace (16, 28) or the emitter 20, as shown in FIGS. 8 and 9. The brush 32 contains a cap 34 and a plurality of bristles 36 that extend outwardly away from the brush 32. The brush 32 and its bristles may be made of any material that conducts electricity. The cap 34 is preferably composed of metal that conducts electricity and retains the bristles 36 within an interior cavity of the cap 34. The cop 34 may be soldered to the trace (16, 28) or emitter 20, allowing electrical current to flow from the trace (16, 28) or emitter 20, through the cap 34, and outward through the bristles 36 by dispensing ions from the bristles 36 to the surrounding area.

In one embodiment, the bristles of the brush 32 are composed of a thermoplastic polymer imbedded with conductive material that allows the polymer to conduct electricity. For example, the bristles of the brush 32 may be composed of polypropylene or polyethylene and impregnated with carbon. Generally, the bristles of the brush 32 may contain between about 20 to about 80 wt % polypropylene copolymer or polyethylene copolymer, between about 5 to about 40 wt % talc, and from about 5 to 40 wt % carbon black. However, any other resistive, inductive, reactive or conductive plastic or non-metallic material may be utilized for the bristles of the brush 32. The flexible ion generation device 10 may include a stiffening element within the device 10 or located at an end of one of the dielectric layers (12, 14, 30). The stiffening element may include one or more dielectric layers affixed to an adjacent dielectric layer within a trace disposed therebetween.

The device may be positioned and secured in place within a conduit or the housing of the air handler unit, such as a duct, such that the points 22 of the emitters 20 are aligned generally perpendicularly to the direction of the airflow across the device, to prevent recombination of the positively charged ions with the negatively charged ions, if the flexible ion electrode 10 produces both negative and positive ions, as opposed to unipolar ionization of negative ions or positive ions.

The treatment of air by delivery of unipolar or bipolar ionization to an airflow within a conduit according to the systems and methods of the present invention may be utilized for various purposes. For example, application of bipolar ionization to an airflow within an HVAC conduit such as an air handler housing or duct may be utilized to abate allergens, pathogens, odors, gases, volatile organic compounds, bacteria, virus, mold, dander, fungus, dust mites, animal and smoke odors, and/or static electricity in a treated air space to which the airflow is directed. Ionization of air in living and working spaces may reduce building related illness and improve indoor air quality; and additionally can reduce the quantity of outside air needed to be mixed with the treated indoor air, reducing heating and cooling costs by enabling a greater degree of air recirculation.

The flexible ion electrode 10 may be used in a variable refrigerant volume (VRV) system having a shared outdoor heat exchanger and a plurality of individual air handler units. Alternatively, the HVAC system can take the form of a variable air volume (VAV), constant air volume (CAV), variable refrigerant flow (VRF) or other forms of heating, ventilation and air conditioning system.

In typical fashion, the shared outdoor heat exchanger comprises a condenser coil, compressor and fan; the individual air handler units each comprise a fan, expansion valve, heating/cooling coil(s), and a filter; and refrigerant lines connect the shared outdoor heat exchanger to the individual air handler units. Return air from the conditioned space and/or fresh air from an exterior space is treated and delivered to a conditioned air space via the individual air handler units. The outdoor heat exchanger discharges waste heat from the conditioned air space to the ambient surroundings, and/or transfers heat from a cooled zone to a heated zone. The flexible ion device 10 may be mounted after the filter and before the heating or cooling coil. Alternatively, the flexible ion generation device 10 may be mounted adjacent the heat exchanger located within the conduit.

Inlet airflow flows through a conduit such as the housing of the air handler unit or a duct is filtered through a filter such as a mesh, screen, paper, cloth or other filter media. A filtered airflow downstream of the filter is treated by discharge of bipolar ionization 36 from the flexible ion electrode 10 to form an ionized airflow. The flexible ion electrode comprises a stream of negatively charged (−) ions and/or a stream of positively charged (+). The ionized airflow enters the inlet of a fan or blower for delivery to the treated air space, and is optionally heated or cooled by passing across or through a cooling coil or heating element. The coil, filter, ion generator, and fan are optionally mounted within a housing of the air handler unit. Example modes of attachment of the flexible ion electrode include, without limitation, adhesive, hook-and-loop fasteners, straps, screws, clips or other mechanical fasteners, magnetic mounting, and/or mounting brackets or carriers affixed to or through the housing or associated ductwork.

The length and thickness of the flexible ion generation device 10 may vary according to a number of physical or electrical parameters and desires by the user.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. A flexible ion generation device, comprising:
   a first dielectric layer having a top portion, a bottom portion, a top side, a bottom side, a left side, and a right side;
   a second dielectric layer having a top portion, a bottom portion, a top side, a bottom side, a left side, and a right side;
   a trace positioned between the first dielectric layer and the second dielectric layer;
   a plurality of emitters engaged to the trace.

2. The flexible ion generation electrode according to claim 1, wherein the emitter has a first end and a second end, the first end of the emitter is engaged to the trace and the second end extends away from the trace and contains a point for emitting ions.

3. The flexible ion generation device according to claim 1, wherein the trace is composed of copper.

4. The flexible ion generation device according to claim 1, further comprising a connector engaged to the first end of the trace.

5. The flexible ion generation device according to claim 1, further comprising a connector engaged to the second end of the trace.

6. The flexible ion generation device according to claim 1, further comprising a brush, containing a plurality of bristles, wherein the brush is engaged to the trace.

7. The flexible ion generation device according to claim 1, further comprising a brush, containing a plurality of bristles, wherein the brush is engaged to the emitter.

8. A flexible ion generation device, comprising:
   a first dielectric layer having a top portion, a bottom portion, a top side, a bottom side, a left side, and a right side;
   a second dielectric layer having a top portion, a bottom portion, a top side, a bottom side, a left side, and a right side;
   a trace positioned between the first dielectric layer and the second dielectric layer;
   a plurality of emitters engaged to the trace and extending outward from the trace and between the first dielectric layer and the second dielectric layer.

9. The flexible ion generation device according to claim 8, further comprising a point positioned on the emitter for emitting ions.

10. The flexible ion generation device according to claim 8, wherein the second dielectric layer has a plurality of openings that are located over a portion of the emitter for allowing ions to be emitted.

11. The flexible ion generation device according to claim 8, further comprising a brush engaged to the emitter for emitting ions.

12. The flexible ion generation device according to claim 8, further comprising a brush engaged to the trace for emitting ions.

13. The flexible ion generation device according to claim 8, further comprising a second trace engaged to the top portion of the second dielectric layer and a third dielectric layer having a top portion and a bottom portion, wherein the bottom portion of the third dielectric layer is engaged to the second trace and the top portion of the second dielectric layer.

14. The flexible ion generation device according to claim 8, wherein the flexible ion generation device is mounted adjacent a heat exchanger located within a conduit.

15. The flexible ion generation device according to claim 8, wherein the device is mounted inside a VRV/VRF air handling system.

16. A method of producing ions, comprising:
   providing a flexible ion generation device with a first dielectric layer having a top portion, a bottom portion, a top side, a bottom side, a left side, and a right side, and a second dielectric layer having a top portion, a bottom portion, a top side, a bottom side, a left side, and a right side, at least one trace having a first end and a second end, the at least one trace is disposed between the first dielectric layer and the second dielectric layer, and at least one emitter engaged to the trace for dispersing ions;
   mounting the flexible ion generation device within a conduit; and
   positioning the at least one emitter within the airflow within the conduit.

17. The method of producing ions according to claim 16, further comprising a power source engaged to the at least one connector.

18. The method of producing ions according to claim 16, further comprising mounting the device after a prefilter and before a cooling coil.

19. The method of producing ions according to claim 16, further comprising at least one brush engaged to the emitter for dispensing ions.

20. The method of producing ions according to claim 16, further comprising a connector engaged to the first end and the second end of the at least one trace.

* * * * *

UNITED STATES PATENT AND TRADEMARK OFFICE
CERTIFICATE OF CORRECTION

Page 1 of 1

PATENT NO. : 10,322,205 B2
APPLICATION NO. : 15/816027
DATED : June 18, 2019
INVENTOR(S) : Charles Houston Waddell It is certified that error appears in the above-identified patent and that said Letters Patent is hereby corrected as shown below:

On the Title Page

Item (63) Related U.S. Application Data:
Change "Continuation of application No. 15/412,825 filed on Jan. 23, 2017, now Pat. 9,849,208" to
This application is a continuation of application No. 15/412,825 filed on Jan. 23, 2017, now Pat. 9,849,208 which claims benefit of Provisional application No. 62/281,318, filed on Jan. 21, 2016.

Item (60) Related U.S. Application Data:
Delete "Provisional application No. 62/281,318, filed on Jan. 21, 2016".

Signed and Sealed this
Twelfth Day of May, 2020

Andrei Iancu
*Director of the United States Patent and Trademark Office*